US012569614B2

(12) United States Patent
Tsuji et al.

(10) Patent No.: US 12,569,614 B2
(45) Date of Patent: Mar. 10, 2026

(54) PRESSURIZATION-TYPE DRUG INJECTOR HAVING DRUG EXPOSURE PREVENTIVE FUNCTION

(71) Applicant: SK-Electronics CO., LTD., Kyoto (JP)

(72) Inventors: Akihito Tsuji, Kagawa (JP); Naoki Matsuda, Hyogo (JP)

(73) Assignee: SK-Electronics CO., LTD., Kyoto (JP)

( * ) Notice: Subject to any disclaimer, the term of this patent is extended or adjusted under 35 U.S.C. 154(b) by 685 days.

(21) Appl. No.: 17/919,953

(22) PCT Filed: Apr. 20, 2020

(86) PCT No.: PCT/JP2020/017083
§ 371 (c)(1),
(2) Date: Oct. 19, 2022

(87) PCT Pub. No.: WO2021/214838
PCT Pub. Date: Oct. 28, 2021

(65) Prior Publication Data
US 2023/0173166 A1      Jun. 8, 2023

(51) Int. Cl.
A61M 5/142      (2006.01)
A61J 1/14      (2023.01)

(52) U.S. Cl.
CPC ............ A61M 5/142 (2013.01); A61J 1/1412 (2013.01)

(58) Field of Classification Search
CPC .. A61M 5/142; A61M 5/14586; A61M 5/152; A61M 5/165; A61M 2025/0019; A61J 1/1412
See application file for complete search history.

(56) References Cited

U.S. PATENT DOCUMENTS 5,578,002 A * 11/1996 Slettenmark ...... A61M 5/14276
604/65
5,620,420 A * 4/1997 Kriesel ................. A61M 5/152
604/890.1

FOREIGN PATENT DOCUMENTS

JP      H05237194      9/1993
JP      2000511075 A      8/2000
(Continued)

OTHER PUBLICATIONS

International Search Report for related International Application No. PCT/JP2020/017083 mailed Jul. 14, 2020 and its English Translation.
(Continued)

Primary Examiner — Theodore J Stigell
(74) Attorney, Agent, or Firm — Renner, Otto, Boisselle & Sklar, LLP

(57) ABSTRACT

[Problem] The purpose of the present invention is to provide a portable anticancer agent container for preventing exposure and infection to the human body caused by chemical solution leakage that arises during a removal operation of a coupling connector at the time of system cleaning using a cleaning solution. [Solution] Provided is a pressurization-type drug injector having a drug exposure preventive function and having a system cleaning function, the pressurization-type drug injector comprising: a reservoir that has a chemical solution filling opening and a chemical solution discharging opening; a pressurization deformation means that undergoes pressurization and deformation by the injection of a chemical solution and that pushes out the chemical solution by a force caused by restoration of the pressurization and deformation; a flow rate control means that adjusts the flow rate of the chemical solution by resistance; a system cleaning port that includes a cleaning solution injection opening, a chemical solution filling opening, and a liquid discharging opening; and a case that contains therein said reservoir, said pressurization deformation means, and said system cleaning port. The case has openings respectively in the vicinity of the chemical solution filling opening, the system cleaning injection opening, and the chemical solution discharging opening. The chemical solution being filled is filled into the pressurization deformation means from the chemical solution filling opening of the reservoir, and moves from the chemical solution discharging opening of the reservoir to the exterior of the container via the flow rate control means. A cleaning solution is injected from the injection opening of the cleaning port arranged downstream from the flow rate control means, and moves to the exterior of the container. The pressurization-type drug injector hav-
(Continued)

ing a drug exposure preventive function is characterized in that the periphery of the cleaning port is completely covered by a sterile seal, and thus, the cleaning port injection opening is kept clean until use.

13 Claims, 6 Drawing Sheets

(56)                    References Cited

FOREIGN PATENT DOCUMENTS

| JP | 2000237132 A | 9/2000 |
|----|--------------|--------|
| JP | 2002532209 A | 10/2002 |
| JP | 2005532140 A | 10/2005 |
| JP | 2006525827 A | 11/2006 |
| JP | 2015181822 A | 10/2015 |
| JP | 2015536211 A | 12/2015 |
| JP | 2016533860 A | 11/2016 |
| JP | 202018493 A | 2/2020 |
| JP | 202065808 A | 4/2020 |
| WO | 9745150 A1 | 12/1997 |
| WO | 0037137 A1 | 6/2000 |
| WO | 2004006994 A1 | 1/2004 |
| WO | 2004105839 A1 | 12/2004 |
| WO | 2014085396 A1 | 6/2014 |
| WO | 2015042161 A1 | 3/2015 |

OTHER PUBLICATIONS

First Office Action for related Japanese Application No. 2018-201179 mailed May 6, 2022 and its English Machine Translation.

* cited by examiner (a)

Patient: CV port (b)

Patient: CV port

Patient: CV port (a)

(b)

PRESSURIZATION-TYPE DRUG INJECTOR HAVING DRUG EXPOSURE PREVENTIVE FUNCTION

This application is a national phase of International Application No. PCT/JP2020/017083 filed Apr. 20, 2020, the entirety of which is hereby incorporated by reference.

TECHNICAL FIELD

The present invention relates to a pressurized drug injector with an agent exposure prevention function comprising an injection port for a detergent.

BACKGROUND ART

According to the 2013 publication of the National Cancer Center Hospital, the total number of cancer patients in Japan is very high at 862, 452 patients, and therapy is administered nationwide. The three major cancer therapies are currently "operation (surgical therapy)", "drug therapy (chemotherapy)", and "radiation therapy". Other therapies include "IVR (catheter therapy)", "hematopoietic stem cell transplantation", "immunotherapy, "alternative therapy", etc., and depending on the cancer type/stage (status of progression)/patient background, etc., the therapeutic methods described above are administered individually or as a plurality of therapies under the guidance of each specialized physician for each patient.

In particular, chemotherapy has an effect of suppressing the growth of cancer cells or preventing recurrence or metastasis by using an anticancer agent. Cancer may be treated with only one type of anticancer agent, or treated with a combination of several types of anticancer agents. Depending on the type of agent, the agent is administered via oral administration, intravenous drip, subcutaneous injection, or direction administration to an organ. Thus, the objective or the timing of the administration varies depending on the cancer type, stage (degree of progression of pathology), lifestyle, etc. The dosing period is generally divided into several doses over several weeks to several months.

In view of high drug reactivity and excellent therapeutic outcome, the main cancer types for which chemotherapy is often employed include colon cancer (ranked no. 2 by sites) and breast cancer (ranked no. 4 by sites). The primary drug solution dosing schedule in colon cancer chemotherapy often involves repeated administration of biweekly 46 to 48 hour sustained intravenous administration, where the agent is administered using a portable drug solution injection pressurized pump. Further, breast cancer chemotherapy is administered as a daily 15 to 90 minute sustained intravenous administration, primarily through gravity dripping, with 21 to 28 days as one session.

Patients experience the following problems when such drug solutions are sustainedly and repeatedly administered intravenously in a short period of time: (1) since blood vessels are subjected to an injection needle every time, the patients experience pain; (2) movement is restricted due to being connected to an IV route during administration; (3) while intravenous injection uses a peripheral vein of the elbow, wrist, etc., such blood vessels are thin, such that administration of a high concentration of an anticancer agent can result in a severe blood vessel pain due to osmotic pressure; and (4) an intravenous injection may require repeated puncture with an injection needle if the vein is thin or occluded. To alleviate such problems, CV ports have been developed, which are embedded subcutaneously and connected to an instrument, which consists of a metal or resin tank known as a port equipped with a silicon septum (target that enables repeated picture with a Huber needle (needle for dedicated use with the port)), with the tip of a resin tube thinner than a blood vessel known as a catheter inserted into a central vein. Such CV ports are widely used among patients undergoing an anticancer agent therapy. When using a CV port, the Huber needle is used, but when a drug solution is not administered, the needle can be withdrawn to release a patient from an IV line.

Current chemotherapy is administered based on evidence from various clinical trials. It is demonstrated that the therapeutic effects are further enhanced by sustained administration, depending on the anticancer agent. In view of the therapeutic outcomes, a representative cancer chemotherapy is the FOLFOX6/FOLFIRI therapy, a 46 to 48 hour sustained administration of an anticancer agent and the worldwide standard therapy for colon cancer chemotherapy. Depending on the regimen, sustained administration may last 7 days, during which patients are inevitably forced to be at rest through hospitalization due to being connected to an IV route. In recent years, portable balloon drug solution injectors have been developed. Since combined use with a CV port system described above can release a patient from an IV route even during drug solution administration, outpatient or home therapy has started to be adopted.

A widely known anticancer agent administration system is a (portable) pressurized drug injector, which can be carried around with a Huber needle (and connecting tube) passed through it. The Huber needle punctures a surgically implanted drug solution loading port called a CV port through the skin and into the body of the patient, such as at the chest, upper arm, or forearm.

When drug solution injection from a CV port is completed, it is necessary to clean the inside of the CV port (hereinafter referred to as system cleaning) using a detergent (saline or heparinized saline) with a Huber needle to flush the remaining drug solution in the port and catheter. This is in order to prevent thrombus formation caused by reverse blood flow, occlusion within the catheter due to a change in drug composition, and such.

A medical liquid storage container disclosed in Patent Literature 1 is known as a conventional portable pressurized drug injector that is used in administration of an anticancer agent. Such a medical liquid storage container is a pressurized drug injector which expands when a drug solution is introduced into a balloon and pushes the drug solution out of the container by a contraction force of the balloon.

However, in the invention described in Patent Literature 1, to conduct system cleaning after administering a drug solution, it is necessary to detach the tube connector of the pressurized drug injector from the tube connector of the Huber needle, and connect a separately prepared syringe containing saline or heparinized saline (hereinafter, referred to as a detergent containing syringe) to the tube connector of the Huber needle. Such an operation is not only cumbersome for the patient or user, but is also known to increase the risk of infection or lead to leaks of the drug solution or detergent when switching the route connection. In particular, this entails a risk of an anticancer agent flowing out from the route and upon exposure to the human body, result in complications such as damage or injury to the body. Conventionally, unreliable and cumbersome methods such as wearing gloves and careful handling of members to avoid exposure to leaked agents were practiced as means of prevention thereof.

Once injection of an anticancer agent containing drug solution from a portable pressurized drug injector is completed, the pressurized drug injector is generally detached from a connector of a Huber needle. A detergent containing syringe is connected thereto or to unevenly shaped connectable connector (three-way stopcock, Y connector, etc.) that is installed on a route between the pressurized drug injector and the Huber needle in order for a medical practitioner, patient, or family member thereof, etc. (hereinafter, referred to as a user) to perform the system cleaning described above. Since a tube filled with an anticancer agent is connected after being disconnected in such an operation, users are constantly at risk of exposure or spread of anticancer agent or an infection causing factor.

CITATION LIST

Patent Literature

[PTL 1] Japanese Laid-Open Publication No. 2015-181822

SUMMARY OF INVENTION

Technical Problem

Thus, the objective of the invention is to provide a portable pressurized drug injector with an agent exposure prevention function for preventing exposure to the human body to and leakage of a drug solution or detergent, and infection upon system cleaning using a detergent.

Solution to Problem

In order to achieved the objective described above, the present invention provides a pressurized drug injector with an agent exposure prevention function comprising a system cleaning function comprised of a container encasing a drug solution loading inlet for loading a drug solution into a reservoir; a balloon, etc. that stores the drug solution and has a pressure capable of discharging the drug solution (including a tank that can be loaded with an agent and has a pressurizing function); a flow rate controlling pipe for adjusting a flow rate of an agent discharged by pressurization from the balloon, etc. (may be a flow rate controlling tube); a drug solution discharge outlet for discharging the drug solution; a liquid transport filter for preventing contamination by air or bacteria; and a drug solution infusion inlet of a system cleaning port.

The container has an aperture for each of the drug solution loading inlet, the system detergent infusion inlet, and the drug solution discharge outlet, and the drug solution loaded in the balloon moves through the drug solution discharge outlet of the reservoir→the fluid transport filter→flow rate controlling pipe→system cleaning port to the outside via each communication means such as a tube.

Since a pressurized drug injector with an agent exposure prevention function with this configuration is provided with a system cleaning port inside as one unit, it is not necessary to detach a connector installed on a tube, etc. and switch with a detergent containing syringe as had been performed up to this point by a user after completion of drug solution administration. Thus, when a user performs system cleaning on a CV port or the like, there is no leakage of the drug solution or detergent to the outside, leading to the accomplishment of the prevention of exposure of users, every person who handles the present product, and people in the vicinity to the drug solution. Thus, the use of the injector is simple and safe for a patient or user in terms of eliminating the need for excessive prevention or effort to prepare for leakage and careful handling for preventing exposure to an agent.

Since a pressurized drug injector with an agent exposure prevention function with this configuration has each of a drug solution loading inlet for infusing a drug solution and an infusion inlet of a system cleaning port disposed inside a container, drug solution leakage or exposure can be prevented upon loading/infusion of a drug solution or detergent.

Since the drug solution loading inlet and the infusion inlet of the system cleaning port introduce a drug solution and detergent, the ports have a connector function (screw hole) that engages with the tip of a syringe for a medical instrument.

In this configuration of the pressurized drug injector with an agent exposure prevention function, the drug solution loading/infusion inlet of the system cleaning port can be secured to a medical instrument by threaded engagement, which can inhibit internal stresses caused by separation due to repulsive actions generated from infusion pressure at a syringe and each loading inlet at the time of infusion of the drug solution, enabling safe and simple operation.

It is desirable that an aperture of the infusion inlet of the system cleaning port of the container is sealed with a detachable sealing member.

It is of utmost importance to prevent contamination induced by a system cleaning operation (introduction of infection causing bacteria, etc. into the body by an operation).

With this configuration of the pressurized drug injector with an agent exposure prevention function, the infusion inlet of the system cleaning port and the periphery of the aperture are sealed with an antiseptic sealing material to maintain an aseptic state, prevent contamination during connection, and enable a safe system cleaning for the patient up until immediately before the system cleaning occurs.

A pressurized drug injector with an agent exposure prevention function with this configuration can adjust the flow rate of agent in accordance with the objective of use regardless of the property of the agent or patient and can be applied broadly to various agents and patients, with excellent portability. If the flow rate is controlled between a balloon and an agent discharge outlet, and an injection inlet of a system cleaning port is provided downstream of a flow rate controlling pipe, the internal pressure increases on the upstream side due to resistance of the flow rate controlling pipe when a drug solution is infused from a system cleaning infusion inlet. Since the downstream side is connected to the vein through a CV port implanted in a patient, a detergent cannot move upstream of a flush port due to the difference in pressure. Therefore, the detergent flows downstream to enable system cleaning.

It is desirable to provide a liquid transport filter for suppressing passage of air and particles with a size that is equal to or greater than a predetermined size, immediately before a flow rate controlling pipe. The liquid transport filter comprises hydrophobic and hydrophilic membranes.

Since a pressurized drug injector with an agent exposure prevention function with this configuration is provided with a liquid transport filter on a flow channel through which an agent passes, the injector enables more simple and safe dosing with excellent portability for a patient without separately preparing a fluid transport filter.

A tube is used as communication means for each of drug solution discharge outlet, fluid transport filter, flow rate controlling pipe, and system cleaning port disposed within the container. It is preferable to comprise a substantially cylindrical tube wrapping section with a spiral notch on the outer circumference, around which the tube can be wrapped. With such a configuration, a tube can be placed within the container so that a compact pressurized drug injector with an agent exposure prevention function can be provided, even when a long tube is used.

The pressurized drug injector with an agent exposure prevention function of the invention can prevent exposure of a user or people in the vicinity to a drug solution or detergent without leakage to the outside when the user is cleaning the system, and prevent leakage or exposure when loading a drug solution or detergent into the pressurized drug injector with an agent exposure prevention function. For this reason, this is beneficial for a user in terms of alleviating the mental burden due to wearing of gloves or careful operation for preventing exposure.

For a pressurized drug injector with an agent exposure prevention function with this configuration, all drug solution infusion inlets can be secured with a medical syringe by threaded engagement when introducing a drug solution or detergent, which can suppress separation due to a repulsive force of a drug solution upon infusion to enable safe and simple operation.

For the pressurized drug injector with an agent exposure prevention function of the invention, a flexible and strong resin container absorbs impact so that the impact or tension is not directly applied to a balloon containing a drug solution, etc. due to mishandling by a user such as dropping during administration of the drug solution. Even if a balloon is damaged to result in leakage of the solution, the drug solution would not leak out of the container due to using a hydrophobic air filter.

With such a configuration, exposure of a user and people in the vicinity can be prevented. Even when dropped, a drug solution loading inlet and system cleaning port inside are not directly impacted, and damage can be prevented.

DESCRIPTION OF EMBODIMENTS

The pressurized drug injector with an agent exposure prevention function of the invention is described hereinafter with reference to the drawings.

Figure 1:
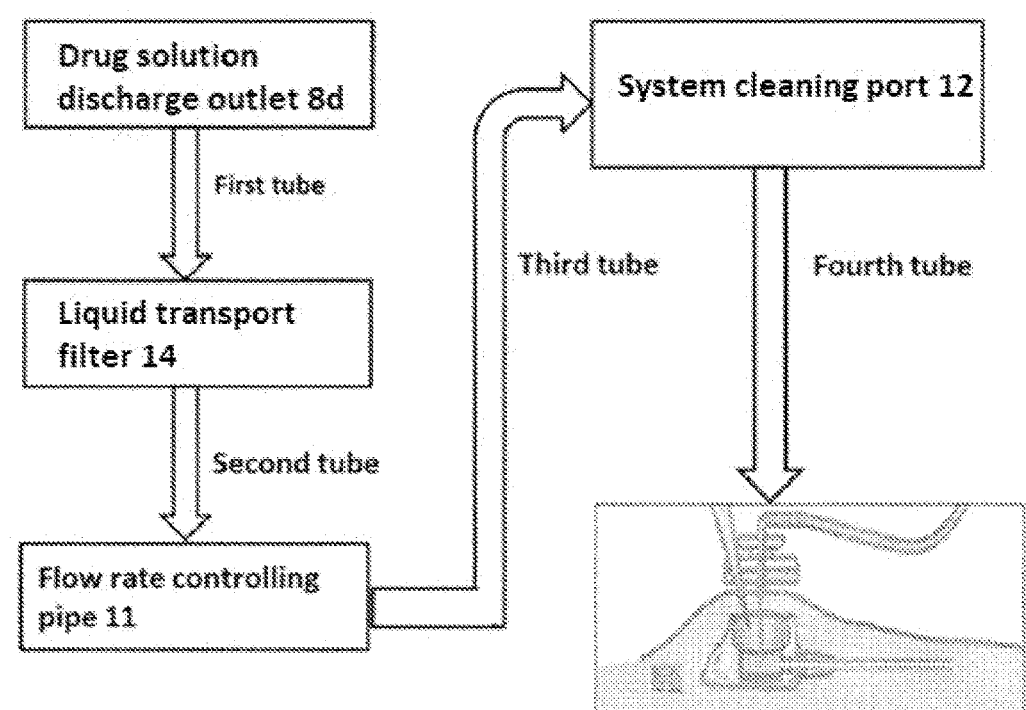
FIG. 1 shows an exemplary schematic diagram of a flow channel for a drug solution in the pressurized drug injector with an agent exposure prevention function of the invention.
Figure 1:
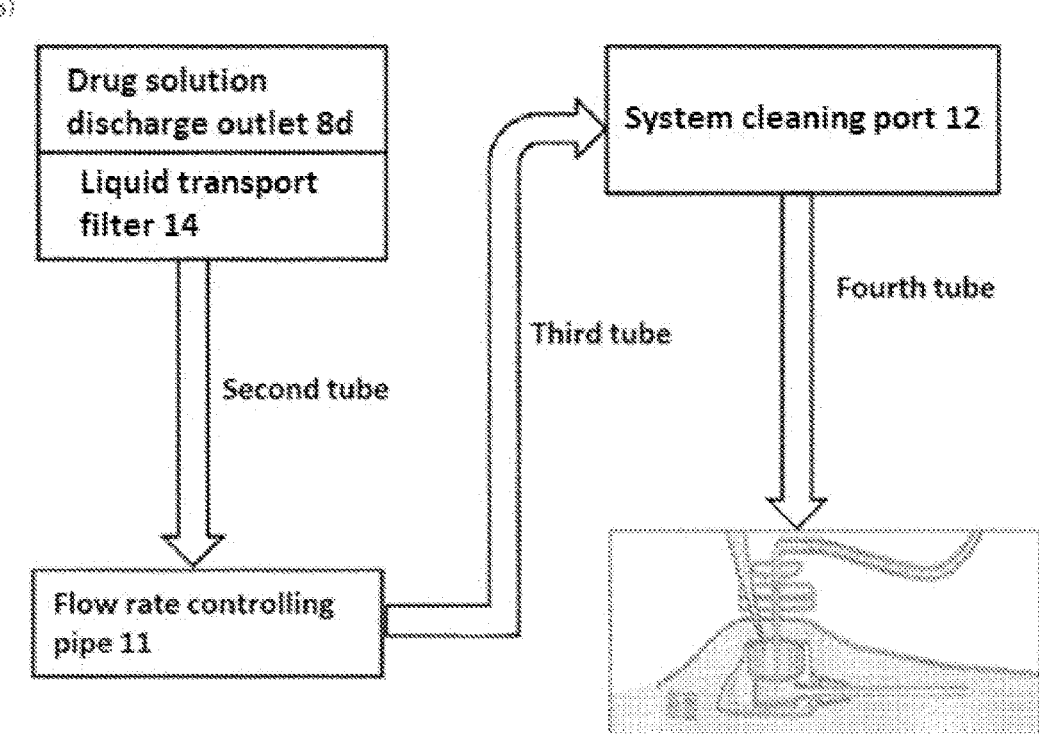
Figure 2:
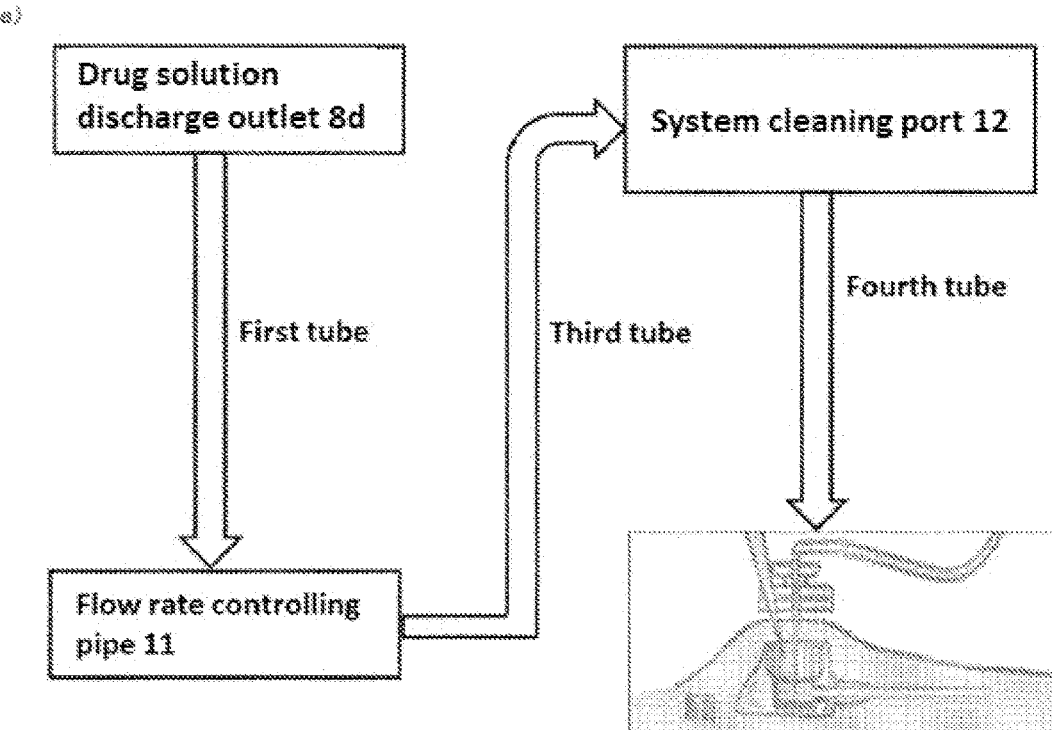
FIG. 2 shows another schematic diagram of a flow channel for a drug solution in the pressurized drug injector with an agent exposure prevention function of the invention.
Figure 2:
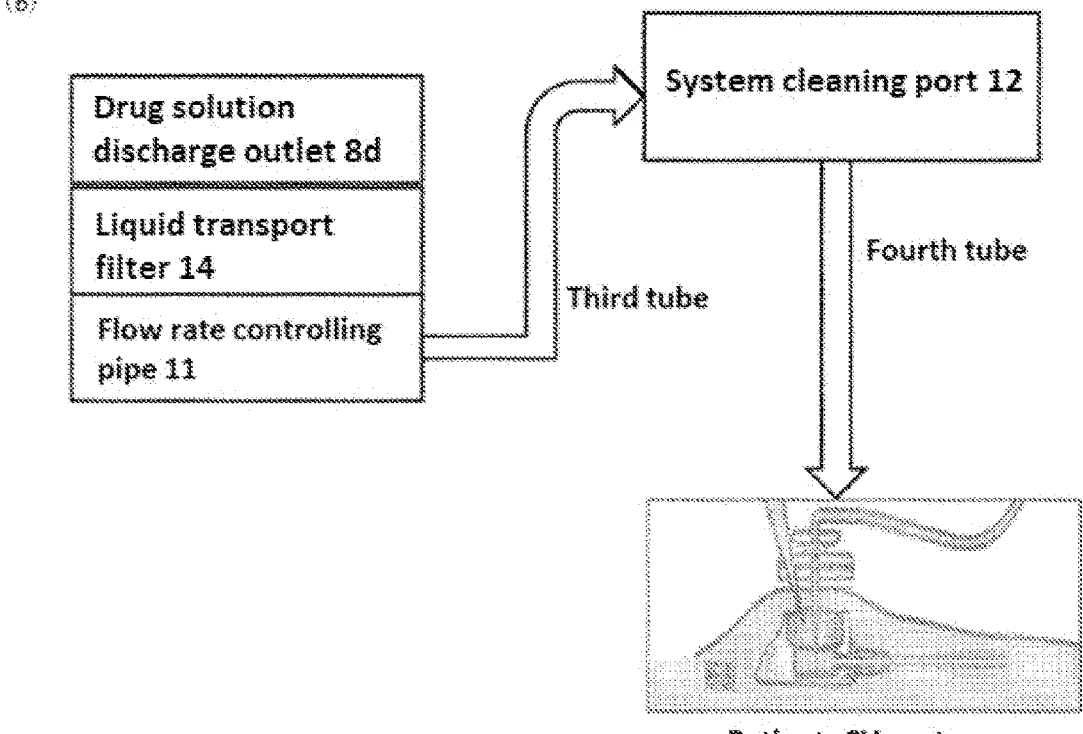
Figure 3:
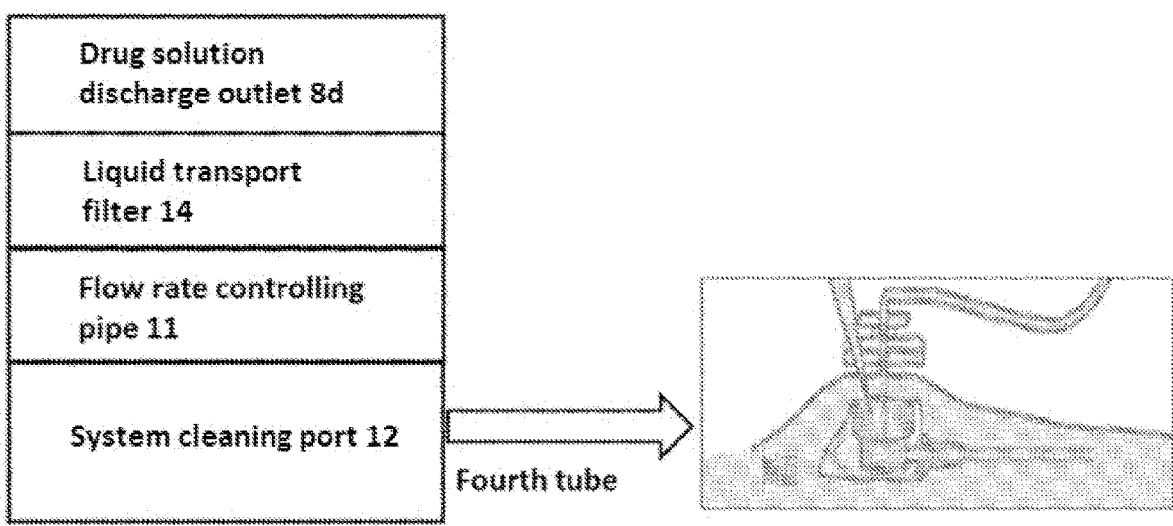
FIG. 3 shows yet another schematic diagram of a flow channel for a drug solution in the pressurized drug injector with an agent exposure prevention function of the invention.

FIGS. 1, 2, and 3 are exemplary schematic diagrams showing a flow channel for a drug solution and detergent of a specific configuration example (see FIGS. 4 to 6) of the pressurized drug injector with an agent exposure prevention function of the invention. A pressurized drug injector with an agent exposure prevention function is described in detail by using the schematic diagrams in FIGS. 1, 2, and 3. The name of each member is described in detail after describing the flow channel.

Figure 4:
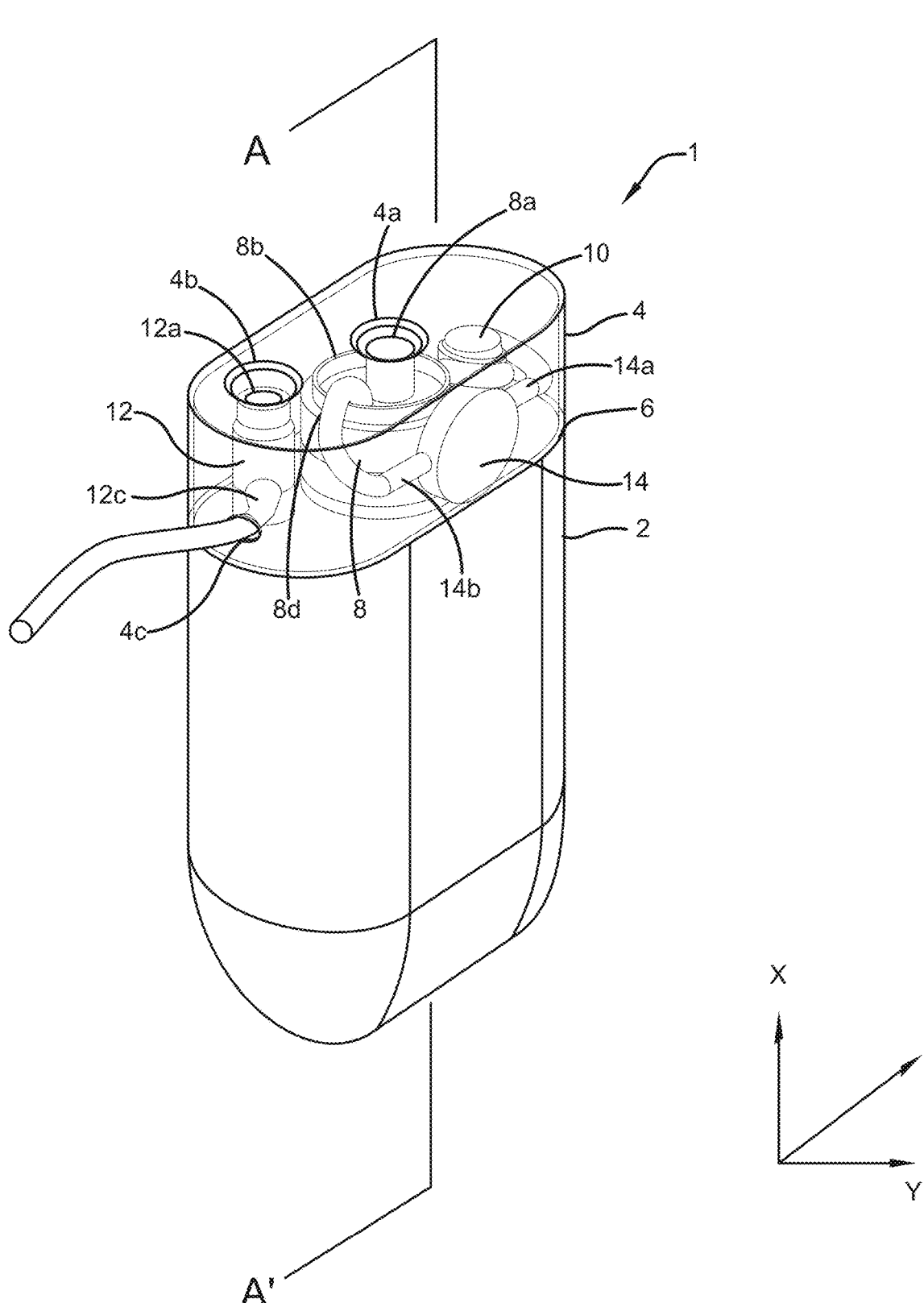
FIG. 4 shows a perspective view of an example of the pressurized drug injector with an agent exposure prevention function of the invention.
Figure 5:
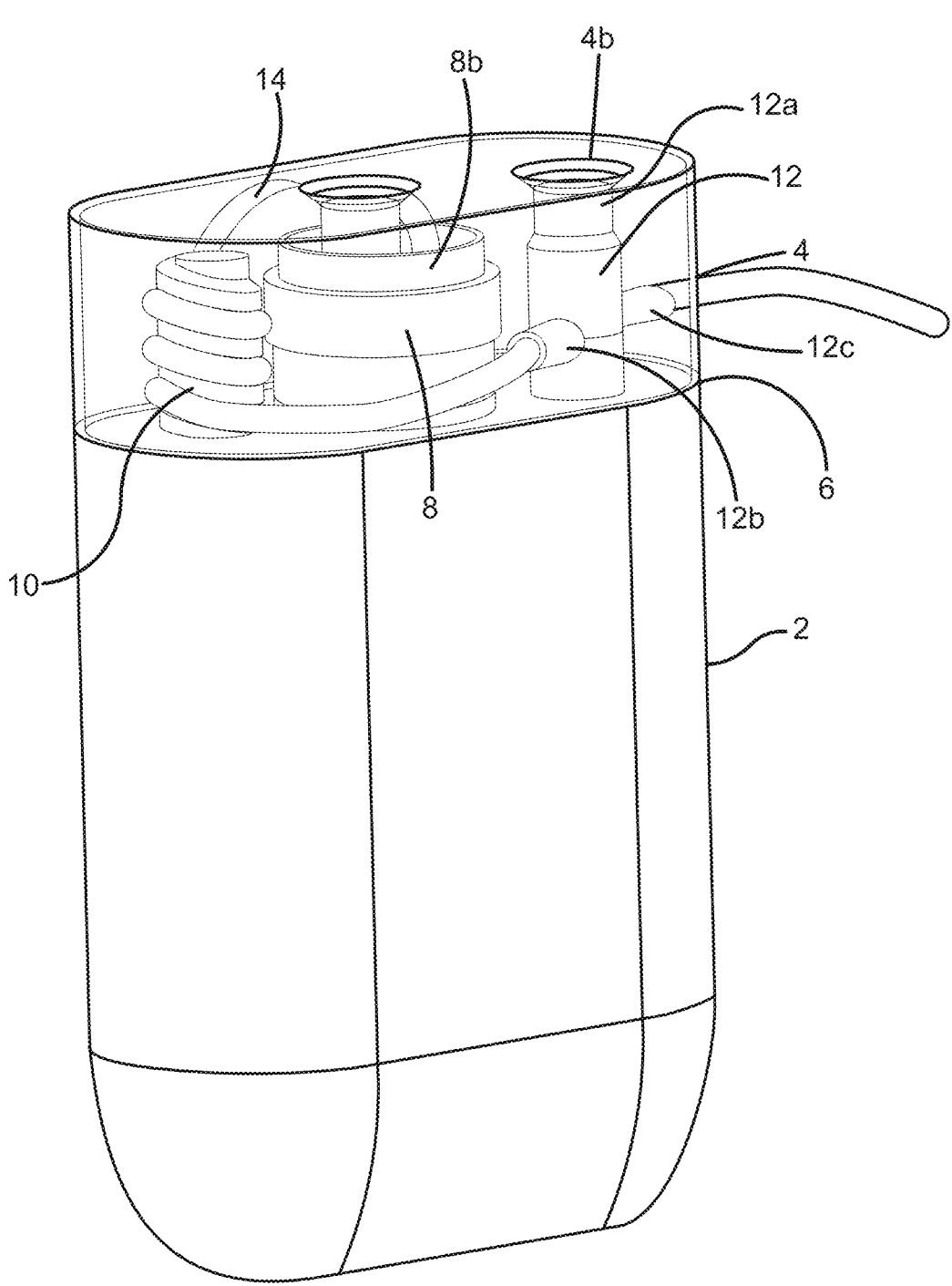
FIG. 5 shows a perspective view seen from the back side of FIG. 4.
Figure 6:
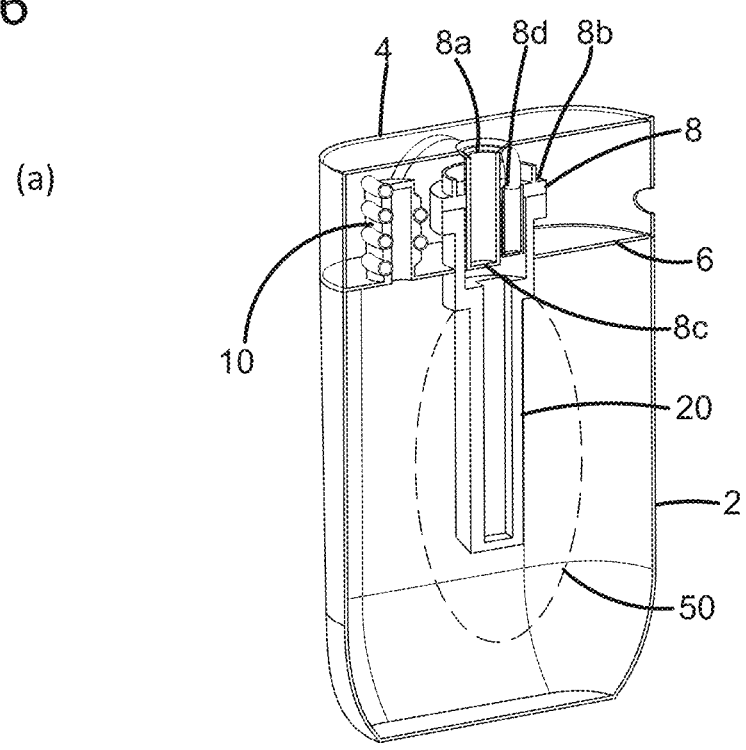
FIG. 6(*a*) shows a cross-sectional perspective view of one side of the pressurized drug injector with an agent exposure prevention function cut at the A-A' cross-section in FIG. 4, and FIG. 6(*b*) shows a cross-sectional perspective view of the other side of the pressurized drug injector with an agent exposure prevention function cut at the A-A' cross-section in FIG. 4.
Figure 6:
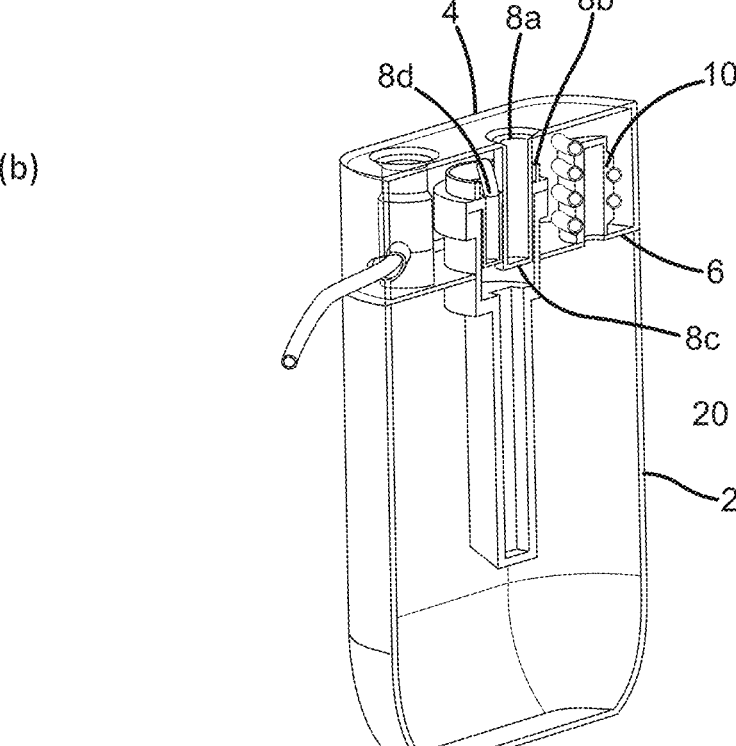

FIGS. 1(*a*) and (*b*), FIGS. 2(*a*) and (*d*), and FIG. 3 show an exemplary flow channel of a pressurized drug injector with an agent exposure prevention function 1, which are embodiments of the present invention shown in FIGS. 4 to 6. According to the flow channel in FIG. 1(*a*), a drug solution is loaded into a balloon 50 from a drug solution loading inlet of the pressurized drug injector with an agent exposure prevention function 1, then moves from a drug solution discharge outlet 8*d* of a reservoir 8 to a liquid transport filter 14 via a first tube, moves from the liquid transport filter 14 to a flow rate controlling pipe 11 via a second tube, moves from the flow rate controlling pipe 11 to a system cleaning port 12 having a detergent infusion inlet (not shown) for introducing a detergent via a third tube, and moves to a patient: CV port via a fourth tube (not shown). In this regard, if a flow rate controlling tube is used in place of the flow rate controlling pipe 11, the flow rate controlling tube can be used from the second tube to the third tube.

A flow rate controlling tube is a tube that adjusts the flow rate with friction from unevenness inside of the tube. The dosing rate of an agent can be adjusted to any value by adjusting the length to any value.

Meanwhile, when the flow rate controlling pipe 11 is used, maneuvering of a tube does not need to be considered, and members can be placed stably. Thus, useless space can be reduced to prepare a pressurized drug injector with an agent exposure prevention function 1 with excellent portability.

The pressurized drug injector with an agent exposure prevention function 1 of the invention is a configuration comprising the drug solution discharge outlet 8*d* to the tube downstream of the system cleaning port 12 within the flow channel described above as one unit. With such a configuration, system cleaning does not require a route switching operation for infusion a detergent, such as detaching the pressurized drug injector with an agent exposure prevention function 1 and a Huber needle or using another connection system, and is simple, so that exposure of the body of a user, etc. to a drug solution can be prevented.

The liquid transport filter 14 is integrated with the drug solution discharge outlet 8*d* in the flow channel of FIG. 1(*b*). In such a case, the first tube is no longer needed, while the second tube is directly communicative from the liquid transport filter 14 to the flow rate controlling pipe 11, and the drug solution moves from the fourth tube to a patient via a CV port. With such a configuration, the pressurized drug injector with an agent exposure prevention function 1 has a small unit size and light weight, so that the injector would have excellent portability.

If a flow rate controlling tube is used in place of the flow rate controlling pipe 11 in the flow channel of FIG. 1(*b*) in the same manner as the flow channel of FIG. 1(*a*), the flow rate controlling tube can be used from the second tube to the third tube.

A configuration that does not use the liquid transport filter 14 as shown in FIG. 2(*a*) may also be used. With such a configuration, the pressurized drug injector with an agent exposure prevention function 1 has a small unit size and light weight, so that the injector would have excellent portability. In the flow channel in FIG. 2(*a*), a drug solution moves from the drug solution discharge outlet 8*d* to the flow rate controlling pipe 11 via a first tube, moves from the flow rate controlling pipe 11 to the system cleaning port 12 having a detergent infusion inlet for introducing a detergent via a third tube, and moves from a fourth tube to a patient via a CV port. In this regard, if a flow rate controlling tube is used in place of the flow rate controlling pipe 11, the flow rate controlling tube can be used from the first tube to the third tube.

The drug solution discharge outlet 8*d*, the liquid transport filter 14, and the flow rate controlling pipe 11 are integrated in the channel of FIG. 2(*b*). The first tube and the second tube are no longer needed, while the third tube is directly communicative with the system cleaning port 12, and the drug solution moves to a patient: CV port via the fourth tube. With such a configuration, the pressurized drug injector with an agent exposure prevention function 1 has a small unit size and light weight, so that the injector would have excellent portability.

The drug solution discharge outlet 8*d*, the liquid transport filter 14, the flow rate controlling pipe 11, and the system cleaning port 12 are integrated in the channel of FIG. 3. The first tube, the second tube, and the third tube are no longer needed, and the drug solution moves to a patient: CV port via the fourth tube. With such a configuration, the pressurized drug injector with an agent exposure prevention function 1 has a small unit size and light weight, so that the injector would have an advantage of having excellent portability.

The pressurized drug injector with an agent exposure prevention function 1 employing the flow channel of FIG. 1(*b*), 2(*a*), 2(*b*), or 3 can be considered as a configuration comprising at least from a drug solution loading inlet for loading a drug solution in a balloon to the drug solution discharge outlet 8*d* to the tube downstream of the system cleaning port 12 as one unit in the same manner as FIG. 1(*a*).

Specific configuration examples of the pressurized drug injector with an agent exposure prevention function 1 of the invention described above are now described using FIGS. 4 to 6.

FIGS. 4 and 5 are perspective views showing an example of the pressurized drug injector with an agent exposure prevention function 1 of the invention. FIG. 5 shows a rear view of FIG. 4 (far side of the drawing). The pressurized drug injector with an agent exposure prevention function 1 of the invention shown in FIGS. 4 and 5 is generally comprised of an exterior case 2, upper cover 4, reservoir 8, tube wrapping section 10, system cleaning port 12, and liquid transport filter 14, as well as the drug solution connecting pipe 20 and balloon 50 shown in FIG. 6.

The exterior case 2 is rectangular with the cross-section in z direction as illustrated having an r-shaped corner, and is formed in a shape that tapers from the lower end to the bottom surface. Thus, the exterior case as a whole has corners reduced to have a shape that is safe and does not get caught when placed in a pocket of a garment of a patient, etc. The upper cover 4 is rectangular with the cross-section in the z direction having an r-shaped corner just like the exterior case 2, and is formed to comprise a top panel and be opened downward, and is covered on and coupled to the upper part of the exterior case 2. A substantially flat top panel 6, which is the top part of the exterior case 2, is disposed between the exterior case 2 and the upper cover 4, and a gap (space) is provided between the exterior case 2 and the top panel 6 and between the upper cover 4 and the top panel 6.

A container consisting of the exterior case 2 and the upper cover 4 is formed with a light material such as resin and has excellent portability. An elastic material is used in the examples of FIGS. 4 to 6 in order to prevent breakage or damage from impact or external tension such as dropping.

On the top panel 6, the tube wrapping section 10, reservoir 8, and system cleaning port 12 are disposed substantially in series in the longitudinal direction of the top panel 6, which are disposed so that the top ends of the tube wrapping section 10, reservoir 8, and system cleaning port 12 would not interfere with the top panel of the upper cover 4. Substantially circular apertures 4*a* and 4*b* are provided on the top panel of the upper cover 4. The drug solution loading inlet 8*a* of the reservoir 8 and a detergent introducing section 12*a* of the system cleaning port 12 can fluidly connect to a medical syringe when introducing a drug solution and detergent. A substantially circular aperture 4*c* for allowing a tube to pass through for discharging a drug solution or detergent to the outside is provided on the side in the vicinity of the system cleaning port 12 of the upper cover 4.

With such a configuration, the pressurized drug injector with an agent exposure prevention function 1 can be readily stored in a pouch or bag, enables dosing while keeping the injector in a pocket of a garment, and can be readily transported by a patient. As described in detail below, a system cleaning port for introducing a detergent is inside the pressurized drug injector with an agent exposure prevention function 1. Thus, the pressurized drug injector with an agent exposure prevention function 1, a drug solution and detergent route switching operation for system cleaning or infusion is not required, so that cleaning can be performed while avoiding exposure or infection due to unexpected leakage.

The reservoir 8 is integrally formed with the drug solution connecting pipe 20 shown in FIG. 6 and penetrates through the top panel 6 of the exterior case 2. The drug solution loading inlet 8*a* is disposed on the top side of the top panel 6 of the reservoir 8, and the aperture 4*a* for connecting to the drug solution loading inlet 8*a* is formed on the upper cover 4.

Meanwhile, the drug solution connecting pipe 20 integrally formed with the lower reservoir 8 of the top panel 6 is disposed in a space between the exterior case 2 and the top panel 6, and the balloon 50 is mounted so as to cover the pipe.

The material is preferably resin, which has a certain level of elasticity to prevent the injector from being readily damaged upon dropping. When loading a drug solution, the drug solution (not shown) is infused into the drug solution connecting pipe 20 shown in FIG. 6 via the aperture 4*a* of the upper cover 4 and the drug solution loading inlet 8*a* from a syringe, etc. (not shown) which is manually handled by a medical practitioner or mechanically controlled. While not illustrated, a check valve 8*c* is disposed between the drug solution loading inlet 8*a* and a reservoir column, so that there is no reverse flow to the drug solution loading inlet. A dedicated screw plug (not shown) is installed in the drug solution loading inlet 8*a*.

Another example of the drug solution loading inlet 8*a* (not shown) includes a screw hole that engages with the tip of a medical syringe for introducing a drug solution into the balloon 50. The tip of a medical syringe having a screw lock is secured to the drug solution loading inlet 8*a* while rotating by threaded engagement, which enables suppression of a repulsive effect generated from resistance of a drug solution and prevention of separation of the drug solution loading inlet 8*a* and the medical syringe upon loading of the drug solution. This also enables stable loading of a drug solution.

For example, a detachable cap (not shown) is provided by threaded engagement at the aperture 4a of the upper cover 4. By removing the cap when introducing an agent and attaching the cap before and after introducing an agent, contamination of the aperture 4a before a drug solution loading operation can be prevented, contamination inside the pressurized drug injector with an agent exposure prevention function 1 during drug solution loading can be prevented, and an agent remaining at an aperture can be sealed off when detaching a medical syringe, etc. It is preferable that a cap is attached to the exterior case 2 or the upper cover 4 with a strap, etc. so that the cap would not be lost during use.

The structure of the reservoir 8 is further described with reference to FIG. 6. FIG. 6 shows a diagram from cutting FIG. 4 at the A-A' cross-section (x-z cross section). FIG. 6(*a*) shows a diagram viewed from the near side of the drawing of FIG. 4, and FIG. 6(*b*) shows a diagram viewed from the far side of the drawing. From the top side, the drug solution loading inlet 8a, receiving section 8b, check valve 8c, drug solution connecting pipe 20, and drug solution discharge outlet 8d integrally form the reservoir 8 as show in FIG. 6. A medical practitioner connects the tip of a medical syringe, etc. to the drug solution loading inlet 8a, applies a positive pressure to allow a drug solution to pass through the check valve 8c, and loads the balloon 50 from the drug solution connecting pipe 20 connected to the balloon. A drug solution loaded into the balloon 50 is completely prevented from flowing in reverse to the drug solution loading inlet 8a by the check valve 8c, so that an agent can be sent out to the drug solution discharge outlet 8d.

The balloon 50 is disposed between the exterior case 2 and the top panel 6, covers the drug solution connecting pipe 20 of the reservoir 8, and is secured so that a loaded agent would not leak.

As the material of the balloon 50, resin rubber such as silicon rubber, which has drug and pressure resistance performance as well as elasticity, is used. When a drug solution is loaded into the balloon 50, the balloon is pressurized and deformed. The drug solution can be pushed upward by a restoration force from the pressure and deformation, whereby the drug solution is sent out to the drug solution discharge outlet 8d via the drug solution connecting pipe 20.

The dotted line in FIG. 6 indicates an expanded state of the balloon 50 from loading a drug solution. The balloon 50 expands within the space in the exterior case 2. When the balloon contracts back to the original size, the enclosed drug solution is pushed upward of the balloon.

Besides balloons, a driving method such as a motor, air pressure, or spring may be used as the pressurizing/deforming means.

A first tube is connected to the drug solution discharge outlet 8d and connected to an infusion inlet 14a of the liquid transport filter 14, and a flow rate controlling tube is connected to the discharge outlet 14b of the liquid transport filter 14. Since 5 to 10 cm of flow rate controlling tube is required, the tube is wrapped around the substantially cylindrical tube wrapping section 10 without bending the tube and is connected to an port inlet 12b of the system cleaning port 12. A fourth tube is connected to a discharge outlet 12c of the system cleaning port 12, and the fourth tube extends out of the container from a aperture 4C of the upper cover 4.

The tube wrapping section 10 preferably comprises a spiral and round groove on the outer circumference and is made of a light resin with elasticity to facilitate wrapping a flow rate controlling tube therearound and prevent the tube from collapsing or bending.

The liquid transport filter 14 is provided in the vicinity of the inside side surface in the longitudinal direction of the upper cover 4. As the shape thereof, a common shape is used. FIGS. 4 to 6 show a substantially circular shape. The liquid transport filter 14 filters a drug solution. It is preferable to use such a filter because contamination of a patient and occlusion of the flow rate controlling pipe 11 or flow rate controlling tube can be prevented when a loaded drug solution is contaminated with a foreign object, particles with a large diameter, or air.

Another example (not shown) of the configuration from the drug solution discharge outlet 8d to a port inlet 12b can be a configuration wherein the drug solution discharge outlet 8d and the port inlet 12b are communicative with the flow rate controlling pipe 11. With such a configuration, the drug solution discharge outlet 8d and the port inlet 12b can be connected directly with the flow rate controlling pipe 11 without a tube interposed therebetween. The required space would be smaller for the amount not used by a tube. Thus, the size of the entire pressurized drug injector with an agent exposure prevention function 1 can be further reduced. A flow rate controlling pipe in this regard refers to those that can control the flow rate by placing a resistive system such as unevenness or filter in the pipe. If the liquid transport filter 14 is equipped within a flow rate controlling pipe, contamination of a patient by a foreign object or particles with a large diameter is prevented while further reducing the size of the pressurized drug injector with an agent exposure prevention function 1.

As another example that is not illustrated, a detachable sealing member may be provided to the aperture 4b of the upper cover 4. A sealing member seals the aperture 4b to cover the aperture from the outside. A detergent introducing section 12a can be seen from the aperture 4b and aperture 4b by removing the sealing member upon introduction of a detergent. This configuration can prevent contamination around the detergent introducing section 12a and maintain the flush port 12 in a clean state until system cleaning. In addition to the aperture 4b, the detergent introducing section 12a, aperture 4b, and detergent introducing section 12a may be sealed with a sealing member. In addition to a sealing member, use of the aforementioned cap member is also contemplated as needed.

At the system cleaning port 12, the top part of the detergent introducing section 12a at the top end of the system cleaning port 12 is disposed away from the aperture 4b of the top panel of the upper cover 4 in the same manner as the reservoir 8 described above. This configuration can prevent a drug solution or detergent from leaking out of the pressurized drug injector with an agent exposure prevention function 1, even when mishandled upon introduction of the drug solution or detergent or when the aperture 4b faces the direction of the ground.

The upper cover 4 also increases the effect of alleviating direct impact on the reservoir 8 or system cleaning port 12.

The pressurized drug injector with an agent exposure prevention function 1 of the invention was described above by using FIGS. 4 to 6, but the design may be changed to be suitable for use in a medical setting. For example, the first tube may be connected to the flow rate controlling pipe 11 to eliminate the second tube by removing the filter 14 to improve portability. The filter 14 may also be provided integrally with the reservoir 8. The overall shape of the pressurized drug injector with an agent exposure prevention function 1 can also be more flat or elongated in accordance with the location where the injector is placed.

As yet another example, it is conceivable to make the injector more light weight and compact by providing the detergent introducing section 12*a* of the system cleaning port 12, for example, on the exterior case 2 and providing an aperture on the exterior case 2 to dispose the detergent introducing section 12*a* away from the drug solution loading inlet 8*a*. In addition, a method of disposing the system cleaning port 12 including the detergent introducing section 12*a* within a substantially sealed space is contemplated in order to maintain the sanitary state of the detergent introducing section 12*a* of the system cleaning port 12.

Conventional pressurized drug injectors with an agent exposure prevention function required switching of tube connection, etc. for infusing a detergent upon system cleaning and entailed risk of exposure to a drug solution or infection. The pressurized drug injector with an agent exposure prevention function 1 of the invention comprises the system cleaning port 12 in a substantially sealed space formed by the exterior case 2 and the upper cover 4 as described above. Such a configuration does not require switching of tube connection, etc., and enables loading of a drug solution and infusion of a detergent as a single unit encasing all of the tube, filter, etc. The tube wrapping section 10 allows any length of tube to be tightly disposed without damage in a certain space.

The pressurized drug injector with an agent exposure prevention function 1 of the invention was described above. The arrangement, shape, and size of members are those that are suitable for use of a drug and as a medical instrument and can be modified within a common scope to be compatible with rapidly advancing medicine.

REFERENCE SIGNS LIST

2 exterior case
4 upper cover
6 top panel
8 reservoir
8*d* drug solution discharge outlet
10 tube wrapping section
12 system cleaning port
14 liquid transport filter
20 drug solution connecting pipe
50 balloon

The invention claimed is:

1. A pressurized drug injector, comprising:
a reservoir having a drug solution loading inlet and a drug solution discharge outlet,
pressurizing and deforming means in communication with the reservoir, wherein the pressurizing and deforming means which is pressurized and deformed by loading of a drug solution from the drug solution loading inlet and pushes out the drug solution from the drug solution discharge outlet by a restoration force against pressurization and deformation,
a flow rate controlling pipe for adjusting a flow rate of the drug solution via resistance,
a system cleaning port that is in communication with the flow rate controlling pipe at a location downstream of the flow rate controlling pipe and that has a detergent loading inlet for infusing a detergent, and
a discharge outlet in communication with the system cleaning port and connected to a tube connectable to a port on a patient, wherein the drug solution infused from the drug solution loading inlet is loaded into the pressurizing and deforming means to pressurize and deform the pressurizing and deforming means, and is pushed out from the drug solution discharge outlet by a restoration pressure against pressurization and deformation,
wherein a flow rate of the drug solution is adjusted by the flow rate controlling pipe,
wherein the pressurized drug injector has a flow channel such that the drug solution passes through the system cleaning port with adjusted flow rate and moves from the discharge outlet through the tube to the port and the detergent loaded from the detergent loading inlet also moves from the discharge outlet through the tube to the port, without the drug solution and the detergent flowing out of the flow channel.

2. The pressurized drug injector of claim 1, wherein the drug solution infusion inlet and the detergent loading inlet have, on the inside, a screw hole that engages a tip of a syringe for introducing a drug solution or a detergent.

3. The pressurized drug injector of claim 2, wherein a filter for suppressing passage of a particle with a size that is equal to or greater than a predetermined size is provided between the drug solution discharge outlet and the flow rate controlling pipe.

4. The pressurized drug injector of claim 1, wherein a filter for suppressing passage of a particle with a size that is equal to or greater than a predetermined size is provided between the drug solution discharge outlet and the flow rate controlling pipe.

5. The pressurized drug injector of claim 1, further comprising a case encasing the reservoir, the pressurizing and deforming means, the flow rate controlling pipe and the system cleaning port,
wherein the case has a cover which has respective aperture positioned in the vicinity of each of the drug solution loading inlet, the discharge outlet, and the detergent infusion inlet.

6. The pressurized drug injector of claim 5, wherein the aperture in the vicinity of the detergent infusion inlet of the case is sealed with a detachable sealing member to ensure a sterilized state.

7. The pressurized drug injector of claim 6, wherein a filter for suppressing passage of a particle with a size that is equal to or greater than a predetermined size is provided between the drug solution discharge outlet and the flow rate controlling pipe.

8. The pressurized drug injector of claim 6, wherein the drug solution loading inlet and the detergent infusion inlet have, on the inside, a screw hole that engages a tip of a syringe for introducing a drug solution or a detergent.

9. The pressurized drug injector of claim 5, wherein the aperture in the vicinity of the detergent infusion inlet of the case is disposed away from a top part of the detergent infusion inlet.

10. The pressurized drug injector of claim 9, wherein the drug solution infusion inlet and the detergent loading inlet have, on the inside, a screw hole that engages a tip of a syringe for introducing a drug solution or a detergent.

11. The pressurized drug injector of claim 9, wherein the aperture in the vicinity of the detergent infusion inlet of the case is sealed with a detachable sealing member to ensure a sterilized state.

12. The pressurized drug injector of claim 9, wherein a filter for suppressing passage of a particle with a size that is equal to or greater than a predetermined size is provided between the drug solution discharge outlet and the flow rate controlling pipe.

13. The pressurized drug injector of claim 1, further comprising a check valve disposed between the drug solution loading inlet and the pressurizing and deforming means, wherein the check valve is open when a positive fluid pressure is applied from a side of the drug solution loading inlet and the check valve is closed when a positive fluid pressure is applied from a side of the pressurizing and deforming means.

* * * * *